United States Patent
Wang et al.

(10) Patent No.: US 11,827,677 B2
(45) Date of Patent: Nov. 28, 2023

(54) ANTIMICROBIAL PEPTIDE ID13, PREPARATION METHOD AND USE THEREOF

(71) Applicant: Feed Research Institute, Chinese Academy of Agricultural Sciences, Beijing (CN)

(72) Inventors: Jianhua Wang, Beijing (CN); Bing Li, Beijing (CN); Da Teng, Beijing (CN); Ruoyu Mao, Beijing (CN); Xiumin Wang, Beijing (CN); Ya Hao, Beijing (CN); Na Yang, Beijing (CN)

(73) Assignee: Feed Research Institute, Chinese Academy of Agricultural Sciences, Beijing (CN)

( * ) Notice: Subject to any disclaimer, the term of this patent is extended or adjusted under 35 U.S.C. 154(b) by 309 days.

(21) Appl. No.: 17/078,613

(22) Filed: Oct. 23, 2020

(65) Prior Publication Data
US 2021/0171585 A1    Jun. 10, 2021

(30) Foreign Application Priority Data
Dec. 4, 2019 (CN) .......................... 201911224704.6

(51) Int. Cl.
C07K 14/39  (2006.01)
C12N 1/16   (2006.01)
C12N 15/81  (2006.01)

(52) U.S. Cl.
CPC ............... *C07K 14/39* (2013.01); *C12N 1/16* (2013.01); *C12N 15/815* (2013.01)

(58) Field of Classification Search
None
See application file for complete search history.

(56) References Cited

U.S. PATENT DOCUMENTS

| | | | | |
|---|---|---|---|---|
| 5,631,144 A | * | 5/1997 | Lemoine | ........ C12Y 302/01039 435/254.2 |
| 2017/0058278 A1 | * | 3/2017 | Paldi | .................. C12N 15/8271 |
| 2021/0171585 A1 | * | 6/2021 | Wang | ................ C07K 14/43577 |

FOREIGN PATENT DOCUMENTS

| CN | 102816769 A | 12/2012 |
|---|---|---|
| CN | 107151674 A | 9/2017 |
| CN | 110468143 A | 11/2019 |
| KR | 10-2013-0111854 A | 10/2013 |

OTHER PUBLICATIONS

Choi W-H et al., "Antibacterial Effect of Extracts of Hermetia Illucens (*Diptera stratiomyidae*) Larvae Against Gram-Negative Bacteria", Entomological Research 42:219-226 (2012) (cited in the CN Office Action).

Huang H. et al., Huazhong University of Science and Technology Press, Medical Microbiology, p. 89 (2019), together with an English-language translation (cited in the CN Office Action).

Li Z. et al., "Antibacterial Immunomodulatory Activities of Insect Defensins-DLP2 and DLP4 Against Multidrug-Resistant *Staphylococcus aureus*", Scientific Reports 7:12124 (16 pages) (2017) (cited in the CN Office Action).

Chinese Office Action dated Feb. 1, 2021 received in Chinese Application No. 201911224704.6, together with an English-language translation.

* cited by examiner

*Primary Examiner* — Hope A Robinson
(74) *Attorney, Agent, or Firm* — Scully, Scott, Murphy & Presser, P.C.

(57) ABSTRACT

The present invention provides an antimicrobial peptide ID13 (with a sequence set forth in SEQ ID NO. 1), a preparation method and use thereof. The antimicrobial peptide ID3 is successfully expressed in *Pichia pastoris* using genetic engineering technology. The antimicrobial peptide ID13 of the present invention has an excellent bactericidal activity against Gram-positive bacteria such as *Staphylococcus aureus, Streptococcus pneumoniae*, and *Streptococcus suis*, and has a low hemolytic activity against mouse red blood cells and a low murine macrophage cytotoxicity.

1 Claim, 4 Drawing Sheets

Specification includes a Sequence Listing.

SEQUENCE LISTING

<160> NUMBER OF SEQ ID NOS: 3

<210> SEQ ID NO 1
<211> LENGTH: 40
<212> TYPE: PRT
<213> ORGANISM: Artificial

```
<220> FEATURE:
<223> OTHER INFORMATION: antimicrobial peptide ID13

<400> SEQUENCE: 1

Ala Thr Cys Asp Leu Leu Ser Pro Phe Lys Val Gly His Ala Ala Cys
1               5                  10                  15

Ala Ala His Cys Ile Ala Arg Gly Lys Arg Gly Gly Trp Cys Asp Gly
            20                  25                  30

Arg Ala Val Cys Asn Cys Arg Lys
        35                  40

<210> SEQ ID NO 2
<211> LENGTH: 120
<212> TYPE: DNA
<213> ORGANISM: Artificial
<220> FEATURE:
<223> OTHER INFORMATION: antimicrobial peptide ID13 encoding sequence

<400> SEQUENCE: 2
gctacttgtg acttgttgtc tccattcaag gttggtcacg ctgcttgtgc tgctcactgt    60
attgctagag gtaagagagg tggttggtgt gacggtagag ctgtttgtaa ctgtagaaag   120

<210> SEQ ID NO 3
<211> LENGTH: 149
<212> TYPE: DNA
<213> ORGANISM: Artificial
<220> FEATURE:
<223> OTHER INFORMATION: optimized antimicrobial peptide ID13 encoding
      sequence

<400> SEQUENCE: 3
ccgctcgaga aaagagctac ttgtgacttg ttgtctccat tcaaggttgg tcacgctgct    60
tgtgctgctc actgtattgc tagaggtaag agaggtggtt ggtgtgacgg tagagctgtt   120
tgtaactgta gaaagtaata atctagagc                                     149
```

ANTIMICROBIAL PEPTIDE ID13, PREPARATION METHOD AND USE THEREOF

CROSS REFERENCE TO RELATED APPLICATION

This application claims the benefit of priority from Chinese Application No. 201911224704.6, filed Dec. 4, 2019, the contents of which are incorporated herein by reference.

FIELD OF THE INVENTION

The invention relates to genetic engineering, in particular, to an antimicrobial peptide ID13 and a preparation method and use thereof.

INCORPORATION BY REFERENCE OF SEQUENCE LISTING

The Sequence Listing in the ASCII text file, named as 38905_Sequence_Listing.txt of 2 KB, created on Oct. 13, 2020, and submitted to the United States Patent and Trademark Office via EFS-Web, is incorporated herein by reference.

BACKGROUND OF THE INVENTION

Antimicrobial peptides (AMPs) are endogenous peptides produced by multicellular organisms for protecting the host from invasion of pathogenic microorganisms, since they play a crucial role in the formation of the innate immune system. They usually have the following features: broad-spectrum antimicrobial activities against pathogenic microorganisms including viruses, bacteria, protozoa and fungi (Zasloff et al., 2002), various bactericidal target sites, a different bactericidal mode from existing antibiotics, and wide activities as immunomodulators. As a result, AMPs are considered as one of the most powerful candidates for antimicrobial drugs in the future (Ali Adem Bahar et al., 2013). However, natural antimicrobial peptides have disadvantages such as low antimicrobial activity, high synthesis costs, and toxicities to eukaryotes. Therefore, how to improve their activity and minimize their toxicity has become the current difficulty and hope in the development of antimicrobial peptide drugs. Accordingly, the modification of antimicrobial peptides for higher antimicrobial activity and reduced toxicity has now become a hot research topic.

Antimicrobial peptide DLP4 is an AMP which has a highly effective anti-$G^+$ bacteria activity and produced by *Hermetia illucens* which undergoes immunostimulation by *Staphylococcus aureus* KCCM 40881 (Park et al., 2015). It has a $CS\alpha\beta$ conformation and has a high antimicrobial effect on Gram-positive bacteria, especially methicillin-resistant *Staphylococcus aureus* (MRSA). MRSA ATCC 43300 is continuously passaged under the effective dose of DLP4 subunit for 30 days, and no drug tolerance such as increased MIC was found. Meanwhile, the MIC value of ceftriaxone increased by 256 times (Li et al., 2017). However, DLP4 is limited in clinical applications due to its antimicrobial activity and cytotoxicity. Therefore, a key technical problem to be solved by the present invention is to design and modify DLP4 to improve its antimicrobial activity and reduce cytotoxicity.

SUMMARY OF THE INVENTION

It is an object of the present invention to provide an insect defensin DLP4-derived peptide ID and a preparation method and use thereof.

The present invention provides an insect defensin DLP4-derived peptide ID13 and a preparation method and use thereof include the following steps:

1. Design of the sequence of a derived peptide: on the basis of an insect defensin DLP4, a derivative peptide ID13 is designed according to critical parameters such as the conservative sequence, disulfide bond, charge, and hydrophobicity, wherein the sequence of the derived peptide ID13 is set forth in SEQ ID NO. 1.
2. Codon optimization: the codons of the DNA sequence encoding the antimicrobial peptide ID13 are optimized according to the biased codons of yeast, and a XhoI cleavage site and a Kex 2 cleavage site are added to the 5' end of the optimized gene sequence (SEQ ID NO: 2). A TAA, TAG terminator sequence and a XbaI cleavage site are added to the 3' end of the optimized gene sequence, and a nucleotide sequence set forth in SEQ ID NO. 3 is obtained.
3. The construction of an expression vector: the DNA sequence set forth in SEQ ID NO: 3 and the vector pPICZαA are digested with XhoI and XbaI and then ligated to obtain a recombinant yeast expression vector.
4. Preparation of genetically engineered strain: after linearization, the recombinant expression vector is transformed into *Pichia pastoris* X-33, and a genetically engineered strain with a high expression level is obtained.
5. A method for culturing the above *Pichia pastoris* X-33 genetically engineered strain, including the following steps:
   1) preparation of seed solution: a single colony of a yeast transformant from a YPD plate is picked and seeded in 10 ml YPD liquid medium comprising 100 μg/mL zeocin, cultured with shaking for 18-24 h at 29° C., 250 rpm, then seeded in 200 mL YPD liquid medium with a seeding mount of 1%, cultured with shaking for 16-18 h at 29° C., 250 rpm until its OD600 nm value is 6, and then the seed solution is obtained;
   2) fermentation culture: the above seed solution is added into 2 L basal salt medium with a seeding mount of 10% at 25° C.~29° C., after that, the pH of the medium is adjust to 5.0, and then 9.6 ml PMT1 is added, with the aeration maintained at 8 vvm, rotation rate at 600 rpm and dissolved oxygen maintained at 20% or more;
   3) feeding carbon source: when the dissolved oxygen value starts to decrease slowly and then suddenly rises to 80% or more, a 50% glucose solution with 12‰ PMT1 is added in a fed-batch manner at a rate of 12-24 mL/L/min for 6-8 h, and the rotation rate is increased to 1000 rpm;
   4) methanol induction: after the addition of glucose, the fungus is starved for half an hour, then 100% methanol is added at a rate gradually increased from 1 mL/L/min in the first hour to 6 mL/L/min in the sixth hour, with the rotation rate increased to 1100 rpm and the pH increased to 5.5, the dissolved oxygen maintained at 20% or more until the end of fermentation;

The formula of the basal salt medium used in step 2) is: 45 g glucose, 50 g $NH_4H_2PO_4$, 20 g $K_2SO_4$, 15 g $MgSO_4·7H_2O$, 6 g $KH_2PO_4$, 0.4 g $CaSO_4$ and 1.5 g KOH, and water is added to obtain a volume of 1 L.

6. The present invention also provides a method for purifying a recombinant protein secreted by the *Pichia pastoris* X-33 genetically engineered fungus, including the steps of dialysis desalting, freeze drying, reconstitution and ion exchange chromatography of the fermentation broth.

The present invention uses insect defensin DLP4 as a template to design antimicrobial peptide ID13. By optimizing the antimicrobial peptide ID13 gene sequence and constructing a specific expression vector, the expression of antimicrobial peptide ID13 in *Pichia pastoris* was realized, and a complete purification system was established, which can realize large-scale production, and can be applied to the fields such as development of antimicrobial drugs and feed additives, and has wide applications and market prospects.

DETAILED DESCRIPTION OF THE INVENTION

Figure 1:
FIG. 1 shows the agarose gel electrophoresis detection result of the product of PCR amplification of ID13 gene in Example 2 of the present invention. M: DNA Marker I; 1: ID13 product.

The present invention will be further described in detail below in combination with the examples and drawings, but the embodiments of the present invention are not limited thereto. Unless otherwise specified, the technical means used in the examples are conventional means well known to those skilled in the art, and the raw materials used are all commercially available products.

The following mediums and buffers were used in the examples:

LB medium: tryptone 10 g/L, yeast extract 5 g/L, NaCl 10 g/L; a solid LB medium is prepared by further addition of 2% agarose.

Low-salt LB medium: tryptone 10 g/L, yeast extract 5 g/L, NaCl 5 g/L; a solid low-salt LB medium is prepared by further addition of 2% agar powder.

MH medium: casein hydrolysate 17.5 g/L, beef powder 5 g/L, starch 1.5 g/L.

MHA medium: prepared by further addition of 2% agar powder into solid MH medium.

YPD medium: peptone 20 g/L, yeast extract 10 g/L, glucose 20 g/L; a solid YPD medium can be prepared by further addition of 2% agar powder.

YPDS medium: peptone 20 g/L, yeast extract 10 g/L, sorbitol 182.2 g/L, glucose 20 g/L, agar powder 20 g/L.

BMGY medium (/L): yeast extract 10 g, peptone 20 g, glycerol 10 ml, 13.4% amino acid-free yeast nitrogen source (YNB) 100 ml, 0.02% biotin 2 ml, 1 mol/L phosphate buffer, pH6.0, 100 m L.

For the use of LB medium, low-salt LB, MH, YPD, YPDS and other mediums, please refer to the Invitrogen *Pichia pastoris* manual.

20 mM phosphate buffer (solution A): 0.4654 g $Na_2HPO_4$, 2.9172 g $NaH_2PO_4$, with deionized water added thereto to 950 mL; the above were placed on a magnetic stirrer until completely dissolved and then the pH is adjusted to 6.7, and the volume is adjusted to 1000 mL.

1M NaCl 20 mM phosphate buffer solution (solution B): 0.4654 g $Na_2HPO_4$, 2.9172 g $NaH_2PO_4$, 58.44 g NaCl, with deionized water added to 950 mL; the above were placed on a magnetic stirrer until completely dissolved and then the pH is adjusted to 6.7, and the volume is adjusted to 1000 mL.

PCR and DNA sequencing were used for gene amplification and transformant identification involved in the following examples.

The method for detecting a protein involved in the following examples is Tricine-SDS-PAGE (Schägger H., et al., 2006).

The method for measuring the concentration of a protein involved in the following examples is the Bradford method.

The method for determining the molecular weight of a protein involved in the following examples is the MALDI-TOF MS method.

The method for purifying a protein involved in the following examples is based on ion chromatography.

The fermentation method involved in the following examples is high-density fermentation method.

The strains and plasmids involved in the following examples were shown in Table 1:

TABLE 1

Strains and Plasmids Used in the Test

| Materials and Plasmids | Description of Source |
|---|---|
| *Escherichia coli* DH5α | purchased from Invitrogen |
| *Pichia pastoris* X-33 | purchased from Invitrogen |
| pPICZαA | purchased from Invitrogen |
| pPICZαA-ID13 | synthesized by Sangon Biotech |
| *Pichia pastoris* X-33 ID13 | The present invention |
| *Staphylococcus aureus* CVCC 546 | purchased from CVCC |
| *Staphylococcus Epidermidis* ATCC 12228 | purchased from ATCC |
| *Streptococcus pneumoniae* CVCC 2350 | purchased from CVCC |
| *Streptococcus suis* CVCC 3928 | purchased from CVCC |

Example 1 Design of Antimicrobial Peptide ID13

Based on the sequence of the defensin DLP4, a derivative peptide ID13 is designed. The amino acid sequence is set forth in SEQ ID NO: 1.

Example 2 Obtaining a Gene Fragment of Antimicrobial Peptide ID13

2.1 Optimization and design of antimicrobial peptide ID13 gene expression sequence The codons of the coding gene of antimicrobial peptide ID13 were optimized according to the biased codons of yeast, and a XhoI cleavage site and a Kex 2 cleavage site were added to the 5' end of the optimized gene sequence; a TAA and TAG terminator sequence and a XbaI cleavage site were added to the 3' end of the optimized gene sequence, and the resulted nucleotide sequence of the expression cassette is set forth in SEQ ID NO 3. The above sequence was synthesized by Sangon Biotech (Shanghai) Co., Ltd.

Example 3 Construction of Yeast Recombinant Expression Vector 3.1 The ID13 gene fragment obtained in Example 2 was digested with XhoI and XbaI endonucleases and then the purified fragment was recovered. At the same time, the pPICZαA vector (purchased from Invitrogen) was digested with XhoI and XbaI.

The double-enzyme cleavage system was as follows:

| Reactant | Volume |
|---|---|
| 10 × NEB buffer 3 | 5 μL |
| DNA sample | 43 μL |
| XhoI | 1 μL |
| XbaI | 12 μL |
| Total | 50 μL |

After loading the above enzyme cleavage system, it was placed in a PCR instrument at 37° C. for a reaction of 4 hours, and then detect by 2% agarose gel electrophoresis. Electrophoresis conditions: 120 V, 30 min. The digested product was recovered with a DNA product recovery kit. After the ID13 gene and pPICZαA vector were digested with XbaI and XhoI, the ID13 gene and the linearized pPICZαA vector were ligated with T4 DNA ligase. The ligation system was as follows:

| Reactant | Volume |
|---|---|
| 5 × T4 buffer | 4 μL |
| T4 ligase | 2 μL |
| gene fragment | 2 μL |
| pPICZaA | 12 μL |
| Total | 20 μL |

Ligation conditions: After loading the above ligation system, they were ligated overnight at 16° C. in a PCR instrument.

3.2 Transform the obtained recombinant vector into *E. coli* DH5α; the transformation steps were as follows:
1) 10 μL of ligation product was added to 50 μL of *E. coli* DH5α competent cells, and placed on ice for 30 min;
2) It was heat shocked at 42° C. for 45 s, and immediately placed on ice for 2-3 min;
3) 450 μL of LB low-salt medium preheated at 37° C. was added and the cultivation was resumed at 37° C. at 100 rpm for 1 h;
4) The fungus was re-suspended, and then 100-200 μL thereof was spread on a LB low-salt solid medium comprising 25 μg/mL Zeocin;
6) Cultivation upside down at 37° C. for 12-16 h.

3.3 Identification of *E. coli* DH5α Positive Transformants
A single colony grown on the low-salt LB plate was picked and seeded in 10 mL LB liquid medium (comprising 25 μg/ml zeocin), cultured overnight at 37° C., 250 rpm, and then a positive transformant was identified by colony PCR. The positive transformants verified by specific primers were picked and seeded in 10 mL low-salt LB liquid medium (comprising 25 μg/mL zeocin), cultured overnight at 37° C., 250 rpm, and then 500 μL was taken for sequencing verification.

The positive transformants were picked and verified by fungus solution PCR for confirmation. The PCR system and conditions were as follows:

PCR System:

| Reactant | Volume |
|---|---|
| ddH$_2$O | 16 μL |
| 10 × PCR buffer | 2.5 μL |
| dNTPs | 2 μL |
| Primer F | 0.5 μL |
| Primer R | 0.5 μL |
| Template | 3 μL |
| pfu Taq enzyme | 0.5 μL |
| Total | 25 μL |

PCR Condition:

| | | |
|---|---|---|
| 94° C. | 5 min | |
| 94° C. | 30 s | |
| 58° C. | 30 s | } 28 cycles |
| 72° C. | 40 s | |
| 72° C. | 10 min | |

The PCR product was subjected to 2% agarose gel electrophoresis to detect the band of interest (FIG. 1). The *E. coli* comprising the recombinant expression vector was preserved in a 15% glycerol tube and the plasmid was extracted for linearization and electro-transformation of *P. pastoris*.

Example 4 Construction of Recombinant Yeast Strain Comprising ID13 Gene 4.1 Linearization of Recombinant Vector pPICZαA-ID13
The constitutive recombinant expression vector pPICZαA-ID13 was digested with PmeI. The cleavage system and reaction conditions were as follows:

| Reactant | Volume |
|---|---|
| 10 × NEB buffer 4 | 10 μL |
| PmeI | 2 μL |
| DNA template | 88 μL |
| Total | 100 μL |

Figure 2:
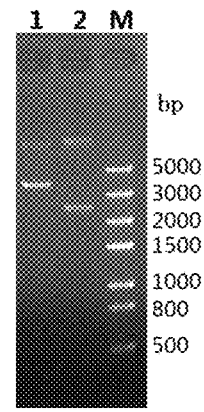
FIG. 2 shows the electrophoresis result of the linearization of the recombinant pPICZαA-ID13 vector in Example 3 of the present invention. M: Trans5K DNA marker; 1: unlinearized recombinant vector pPICZαA-ID13; 2: linearized recombinant vector pPICZαA-ID13.

After loading the above enzyme cleavage system, it was placed in a PCR instrument at 37° C. for a reaction of 4 hours, and then detected by 2% agarose gel electrophoresis. Electrophoresis conditions: 120 V, 30 min. The result of electrophoresis (FIG. 2) showed that the pPICZαA-ID13 recombinant vector was completely linearized.

4.2 Preparation of Competent *Pichia pastoris* X-33
1) A single colony of *Pichia pastoris* X-33 was picked from the YPD plate, seeded into 10 mL YPD liquid medium, and then cultured overnight at 29° C., 250 rpm;

2) *Pichia pastoris* X-33 overnight culture solution was seeded in 100 mL YPD liquid medium with a seeding amount of 1%, and cultured at 29° C., 250 rpm until $OD_{600}$ absorbance value was 1.1-1.3;
3) 50 mL culture was taken and centrifuged at 4° C., 4000 rpm for 5 min, and 50 mL sterile water was added for re-suspension;
4) The culture was centrifuged at 4° C., 4000 rpm for 5 min, the supernatant was removed; 25 mL sterile water was added for re-suspension;
5) The culture was centrifuged at 4° C., 4000 rpm for 5 min; the supernatant was removed; 2 mL of 1M sorbitol was added for re-suspension;
6) The culture was centrifuged at 4° C., 4000 rpm for 5 min; the supernatant was removed, and 2 mL of 1M sorbitol was added for re-suspension; *Pichia pastoris* X-33 competent cells were obtained.

4.3 Electrotransformation

100 μL of yeast competent cells was added to the linearized recombinant plasmid freeze-dried powder, mixed gently, transferred into an ice-chilled electrotransformation cup, placed on ice for 5 min, and electrotransformation was performed with the parameters of 1200V, 25 μF, 400Ω. After the electrotransformation, 1 ml ice-chilled 1M sorbitol solution was added immediately, mixed and transferred into a 2 ml centrifuge tube, and the fungus solution was resuscitated at 29° C. for 2 h; 100 μL of the resuscitated fungus solution was spread on the YPDS plate comprising 100 μg/mL antibiotic zeocin, and was cultured upside down at 29° C. until a single colony growed.

4.4 Induction and Screening of a Positive Transformants in 48-Well Plate

500 μL of BMGY medium was added to each well of the 48-well plate, and half of the single colonies grown in Example 3.3 were picked into the 48-well plate. Blank control wells without fungus, negative control wells with pPICZαA empty plasmid and positive control wells which can definitely be induced were set up. The wells were cultured with shaking at 29° C. and 250 rpm. Methanol (100%) was repeatedly added every 24 h to a final concentration of 0.5% (v/v) during the 72-h induction period. After 72 h induction, the fermentation broths in the 48-well plate were collected separately into a 1.5 mL centrifuge tubes, and then centrifuged to obtain the supernatants which were used for an antimicrobial activity test.

Example 5 High-Density Fermentation of Recombinant Yeast Strains

A single colony of the transformant from the YPD plate was picked and seeded into a 50 mL shake flask with a volume of 10 ml YPD liquid medium (comprising 100 μg/ml zeocin), for cultivation at 29° C., 250 rpm, 18-24 h, then seeded into a 1 L shake flask comprising 200 ml of YPD seed liquid medium with a seeding amount of 1%, at 29° C., 250 rmp, 16-18 h, until an $OD_{600}$ nm was 4-6. The resulting liquid was used as a high-density fermentation seed liquid for later use.

A 5 L fermenter was used for high-density fermentation. The fermentation process was divided into three stages: (1) fungus growth stage: 2 L basal salt medium was added in the fermenter, sterilized at 121° C. for 20 min, cooled to 29° C., with its pH adjusted to 5.0. 9.6 mL PMT1 was added into the fermenter, and then the 200 mL fungus solution (1:10) was seeded, with a ventilation maintained at 8 vvm, a speed of 600 rpm, and the dissolved oxygen maintained at 20% or more; (2) the growth phase during which glucose was added in a fed-batch manner: when the dissolved oxygen value started to decrease slowly and then suddenly rised, 50% glucose solution (12‰ PMT1) was added in a fed-batch manner at a rate of 24 mL/L/min for 6 h continuously, and then the rotation rate was increased to 1000 rpm, without any change of other fermentation conditions; (3) methanol induction phase: fermentation conditions were changed, after the addition of glucose in a fed-batch manner for 6 hours, the fungus was starved for half an hour, then 100% methanol was added complementally at a rate gradually increased from 1 mL/L/min in the first hour to 6 mL/L/min in the sixth hour, with the rotation rate increased to 1000 rpm, the pH increased to 5.5, the dissolved oxygen maintained at 20% or more, without any change of other fermentation conditions, until the end of fermentation.

Figure 3:
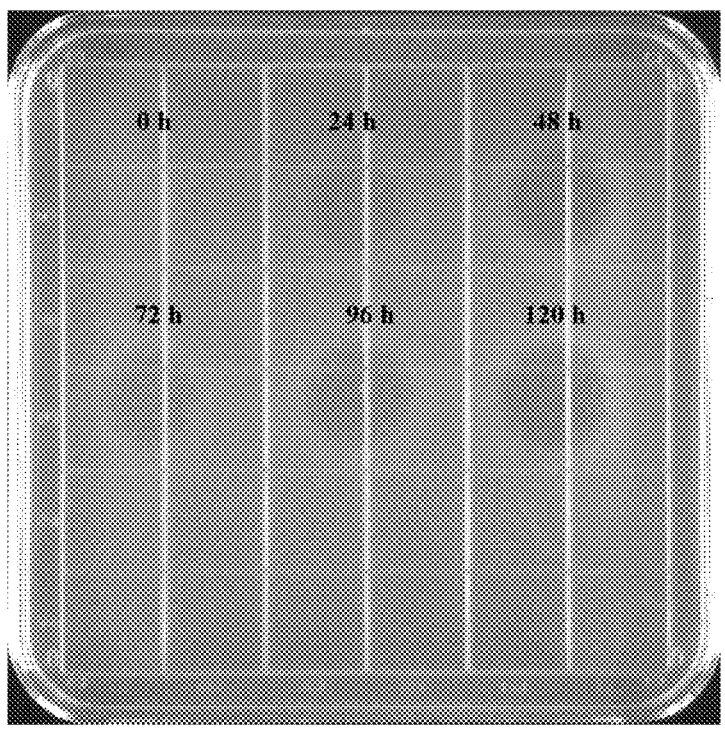
FIG. 3 shows the detection results of the antimicrobial activity of the fermentation supernatant of the ID13 recombinant yeast strain in Example 5 of the present invention at different induction times every 24 h.
Figure 4:
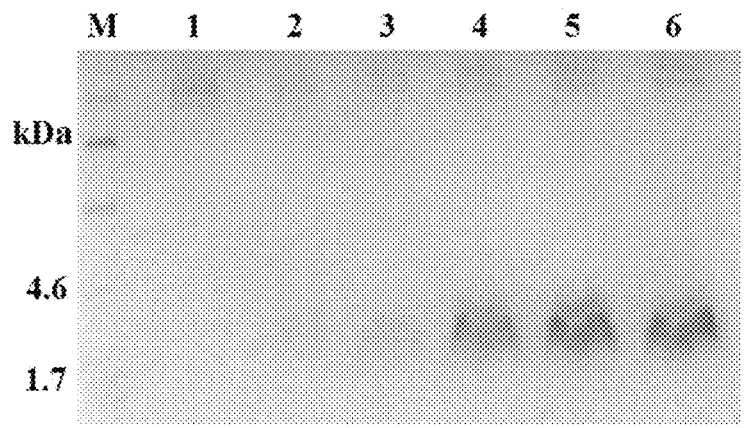
FIG. 4 shows the detection results of the Tricine-SDS-PAGE electrophoresis of the fermentation supernatant of ID13 recombinant yeast strain in Example 5 of the present invention after different times of induction and fermentation. M: ultra-low molecular weight protein marker; 1-6: electrophoresis bands of the supernatant of the fermentation broth at 0 h, 24 h, 48 h, 72 h, 96 h, 120 h after induction, respectively.

Starting from the induction phase, samples were taken every 24 hours for analyzing the protein expression and antimicrobial activity. FIG. 3 showed the antimicrobial effect of the high-density fermentation supernatants of recombinant yeast strains, and FIG. 4 showed the electrophoresis results of the fermentation supernatant protein.

Example 6 Purification of Antimicrobial Peptide ID13

Figure 5:
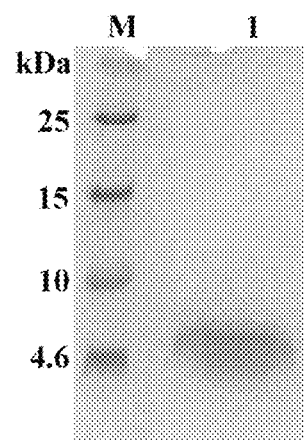
FIG. 5 shows Tricine-SDS-PAGE of the antimicrobial peptide ID13 of Example 6 of the present invention.
Figure 6:
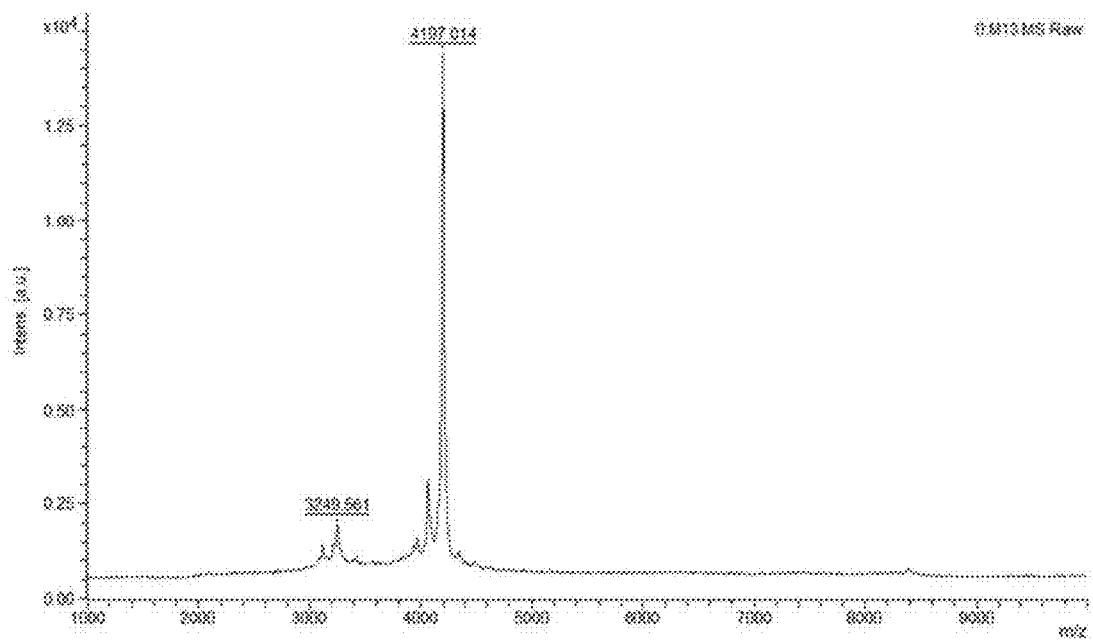
FIG. 6 shows the mass spectrometric identification of the antimicrobial peptide ID13 in Example 6 of the present invention.

The HiPrep SP FF cation exchange column (with a length of 16 mm, an inner diameter of 10 mm, GE Healthcare) was equilibrated with liquid A for 3-5 fold column volumes before loading. After the sample was loaded, the column was eluted with 20 mM phosphate elution buffer, pH 5.7. After the breakthrough peak was eluted completely, a 20 mM phosphate elution buffer (B solution) comprising 0.6 M NaCl, pH 6.7, was used for elution, and the elution peak was collected. The elution situation was monitored at UV280 nm. FIG. 5 showed the purified ID13 Tricine-SDS-PAGE and FIG. 6 showed the purified ID13 mass spectrometry detection. Purified peptide samples were dialyzed against distilled water and lyophilized.

Example 7 Detection of Antimicrobial Peptide ID13's Antimicrobial Activity

The minimum inhibition concentration (MIC) of ID13 against pathogens was measured using a trace broth dilution method. The freeze-dried powder of antimicrobial peptide ID13 obtained in Example 6 was used to prepare a solution of antimicrobial peptide ID13 with a concentration of 1280 μg/mL and a solution of vancomycin, respectively with sterile normal saline, and diluted with a two-fold ratio to a final concentration of 1.25 μg/mL. The antimicrobial peptide ID13 solutions and vancomycin solutions of different concentrations were added to a sterile 96-well cell culture plate, with 10 μL per well, three parallels for each sample, and the same amount (10 μL) of sterile saline was used as a negative control, to prepare MIC plates. Strains were cultured in MH liquid medium with shaking at 37° C. until its OD600 nm=0.4 and diluted to $1 \times 10^5$ CFU/ml. 90 μL of cell suspension was added into each well of the prepared sample well of the MIC plate and incubated at 37° C. for 16-18 h. The test results were recorded and shown in Table 2.

TABLE 2

The antimicrobial activity of ID13 against Gram-positive bacteria

| Species and Strains | MIC | | | | | |
|---|---|---|---|---|---|---|
| | ID13 | | DLP4 | | Vancomycin | |
| | µM | µg/mL | µM | µg/mL | µM | µg/mL |
| | Gram-positive bacteria | | | | | |
| Staphylococcus aureus ATCC 43300 | 0.95 | 4 | 3.75 | 16 | 0.67 | 1 |
| Staphylococcus aureus CVCC 546 | 0.95 | 4 | 3.75 | 16 | 0.67 | 1 |
| Staphylococcus Epidermidis ATCC 12228 | 1.91 | 8 | 1.87 | 64 | 0.67 | 1 |
| Streptococcus pneumoniae CVCC 2350 | 0.95 | 4 | 1.87 | 32 | 0.34 | 0.5 |
| Streptococcus suis CVCC 3928 | 0.95 | 4 | 3.75 | 16 | 0.17 | 0.25 |

Example 8 Hemolysis Assay of Antimicrobial Peptide ID13

Figure 7:
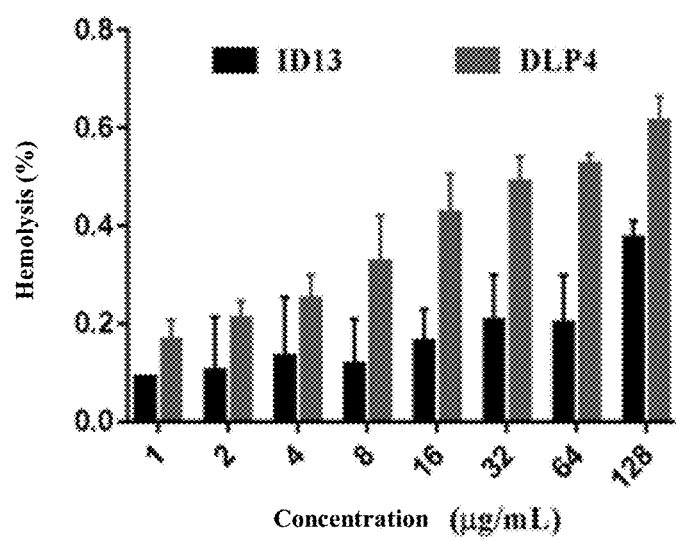
FIG. 7 shows the hemolytic test of the antimicrobial peptide ID13 in Example 8 of the present invention.

The freeze-dried powder of antimicrobial peptide ID13 obtained in Example 6 was used for the test. The antimicrobial peptide ID13 was dissolved in sterile physiological saline to prepare a stock solution of a concentration of 512 µg/mL, and diluted with a 2-fold ratio to a final concentration of 2 µg/mL. The blood from the eyeballs of 6-week-old SPF female ICR mice was taken and collected with a heparin sodium anticoagulation tube. The collected blood was centrifuged at 4° C., 1500 rpm for 10 min. The red blood cells were washed three times with 10 mM PBS (pH 7.3) until the supernatant was colorless and transparent, and an 8% red blood cell suspension was prepared. 100 µL of the red blood cell suspension and antimicrobial peptide ID13 solution were added to 96-well plate, incubated at 37° C. for 1 h, and centrifuged at 1500 rpm for 5 min. The resulted supernatant was transferred to ELISA plate to detect the UV absorbance at 540 nm. Values of 0% and 100% hemolysis control tests were set up with physiological saline and 0.1% TRITON X-100 detergent, respectively. The formula for calculating the degree of hemolysis was as follows (Jung, Park, etc., 2007): Hemolysis (%)=[(Abs540 nm antimicrobial peptide ID13—Abs540 nm physiological saline)/(Abs540 nm 0.1% TRITON X-100 detergent—Abs540 nm physiological saline)]×100%. The result was shown in FIG. 7.

Example 9 Cytotoxicity Assay of Antimicrobial Peptide ID13

Figure 8:
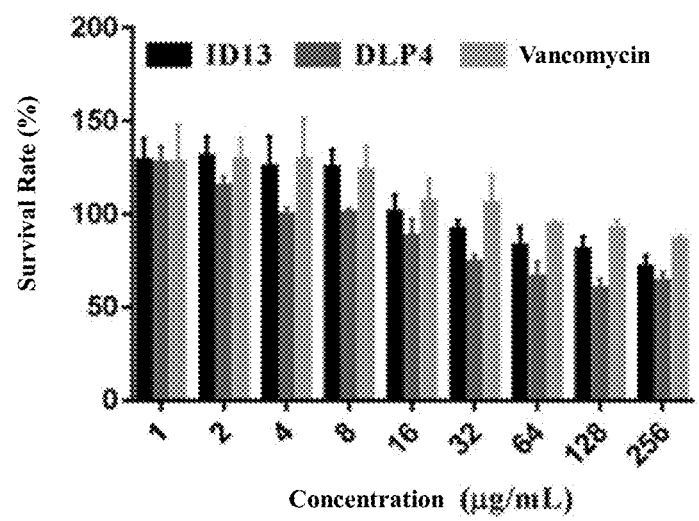
FIG. 8 shows the cytotoxicity test of the antimicrobial peptide ID13 in Example 9 of the present invention.

The RAW264.7 cells were cultured in DMEM complete medium with 37° C., 5% $CO_2$ and saturated humidity conditions. The cells were pipetted and re-suspended in DMEM complete medium. Then, the cells were seeded in a 96-well plate at a density of $2.5×10^5$ cells/mL, 100 µL per well, and 3 replicates were set. After 24 h, the medium was removed, and 100 µL of 1, 2, 4, 8, 16, 32, 64, 128, and 256 µg/mL ID13 were added to each well according to a concentration gradient. Control wells were added with the same amount of PBS solution. After 24 hours incubation, the medium was removed; the wells were washed twice with PBS, and 100 µL of MTT at a concentration of 5 mg/mL was added to each well (which were operated in dark). The 96-well plate was moved to an incubator and continued to be incubated for 4 h. After discarding the MTT solution, 150 µL DMSO was added into each well, and then the plate was cultured with shaking for 10 minutes. When crystals at the well bottom were completely dissolved, the absorbance values were measured at a wavelength of 570 nm. The cell survival rate was calculated according to the following formula: survival rate (%)=OD value of the treatment group/OD value of the control group×100% (Jiao et al., 2015). The result was shown in FIG. 8.

The invention has successfully optimized the antimicrobial peptide ID13 encoding gene, and constructed the pPICZαA-ID13 recombinant expression vector, which is linearized by PmeI and then successfully transformed into Pichia pastoris X-33 to obtain a recombinant yeast strain. The purified antimicrobial peptide ID13 has been tested for antimicrobial activity. The result shows that ID13 has potent antimicrobial activity against Gram-positive bacteria (0.95-1.91 µM), which is significantly better than its parental peptide DLP4 (1.87-3.75 µM). The result of hemolysis test shows that ID13 within a concentration of 1-256 µg/mL has little hemolysis to mice red blood cells. The cytotoxicity test result of ID13 shows that the cell survival rate of ID13 at a concentration of 256 µg/mL is 72%. Therefore, antimicrobial peptide ID13 has a good antimicrobial activity and low toxicity, and is promising to be used for industrial production. Although the general description, specific embodiments and tests have been used to describe the present invention in detail, some modifications or improvements can be made on the basis of the present invention, which would be obvious to those skilled in the art. Therefore, the modifications or improvements made without departing from the spirit of the present invention are within the scope of the present invention.

REFERENCES

1. Bahar A, Ren D. Antimicrobial Peptides [J]. Pharmaceuticals, 2013, 6(12):1543-1575.
2. Li Z Z, Mao R Y, Teng D, et al., Antimicrobial and immunomodulatory activities of insect defensins-DLP2 and DLP4 against multidrug-resistant Staphylococcus aureus [J]. Scientific Reports 7: 12124.
3. Park S I, Kim J W, Yoe S M (2015) Purification and characterization of a novel antimicrobial peptide from black soldier fly (Hermetia illucens) larvae [J]. Developmental and Comparative Immunology 52: 98-106.
4. Zasloff, Michael. Antimicrobial peptides of multicellular organisms [J]. Nature, 2002, 415(6870):389-395.

The invention claimed is:

1. An isolated antimicrobial peptide ID13 comprising the amino acid sequence set forth in SEQ ID NO: 1, wherein the peptide is an insect defensin.

* * * * *